United States Patent
Jang et al.

(10) Patent No.: US 11,273,331 B2
(45) Date of Patent: Mar. 15, 2022

(54) SYSTEMS AND METHODS FOR HIGH INTENSITY FOCUSED ULTRASOUND

(71) Applicant: The Board of Trustees of the Leland Stanford Junior University, Stanford, CA (US)

(72) Inventors: Ji Hoon Jang, Palo Alto, CA (US); George Quintin Stedman, Mountain View, CA (US); Morten Fischer Rasmussen, San Francisco, CA (US); Arif Sanli Ergun, Palo Alto, CA (US); Butrus T. Khuri-Yakub, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/786,641

(22) Filed: Feb. 10, 2020

(65) Prior Publication Data
US 2020/0254285 A1   Aug. 13, 2020

Related U.S. Application Data

(60) Provisional application No. 62/804,626, filed on Feb. 12, 2019.

(51) Int. Cl.
*A61N 7/02* (2006.01)
*A61B 8/00* (2006.01)
*A61N 7/00* (2006.01)

(52) U.S. Cl.
CPC ............ *A61N 7/022* (2013.01); *A61B 8/4488* (2013.01); *A61B 8/4494* (2013.01); *A61B 8/54* (2013.01);
(Continued)

(58) Field of Classification Search
CPC ............ A61N 7/022; A61N 2007/0004; A61N 2007/0052; A61N 2007/0078; A61B 8/4488; A61B 8/54; A61B 8/4494
See application file for complete search history.

(56) References Cited

U.S. PATENT DOCUMENTS 3,636,372 A * 1/1972 Hujita .................. H03K 19/017
327/433
5,823,962 A * 10/1998 Schaetzle .............. B06B 1/0607
600/439

(Continued)

OTHER PUBLICATIONS

Jang, Ji Hoon, et al. "Dual-mode integrated circuit for imaging and HIFU with 2-D CMUT arrays." 2015 IEEE International Ultrasonics Symposium (IUS). IEEE, 2015. (Year: 2015).*

(Continued)

*Primary Examiner* — Sean D Mattson
(74) *Attorney, Agent, or Firm* — Knobbe Martens Olson & Bear LLP

(57) ABSTRACT

Features for high intensity focused ultrasound (HIFU) are described. The application of HIFU for ablating tissue may be monitored in real time by imaging bubbles generated during HIFU. A single transducer array may be used by fast switching between imaging and HIFU. For imaging, the array or portions thereof may be used in receive only mode to locate bubbles generated by the HIFU. The application of HIFU, such as location and/or intensity, may be adjusted based on information from the imaging of the bubbles. Physicians and/or others may use these systems and methods to monitor HIFU procedures in real-time for optimal ablation of target tissue with minimal damage to healthy tissue.

20 Claims, 8 Drawing Sheets

(52) U.S. Cl.
CPC ............... *A61N 2007/0004* (2013.01); *A61N 2007/0052* (2013.01); *A61N 2007/0078* (2013.01)

(56) References Cited

U.S. PATENT DOCUMENTS

| | | | |
|---|---|---|---|
| 5,984,881 A * | 11/1999 | Ishibashi | A61B 17/2256 601/2 |
| 6,488,630 B1 | 12/2002 | Hand et al. | |
| 6,508,774 B1 * | 1/2003 | Acker | A61B 8/0833 600/439 |
| 7,063,666 B2 | 6/2006 | Weng | A61B 17/0057 600/439 |
| 8,568,339 B2 * | 10/2013 | Rybyanets | A61N 7/02 601/2 |
| 8,715,186 B2 * | 5/2014 | Slayton | A61B 8/48 600/437 |
| 10,123,782 B2 | 11/2018 | Bhuyan et al. | |
| 2001/0044278 A1 | 11/2001 | Chiao et al. | |
| 2003/0233044 A1 | 12/2003 | Brock-Fisher | |
| 2005/0113694 A1 | 5/2005 | Haugen et al. | |
| 2008/0228075 A1 * | 9/2008 | Fraser | A61B 17/22004 600/443 |
| 2009/0182233 A1 | 7/2009 | Wodnicki | |
| 2009/0240148 A1 * | 9/2009 | Jeong | B06B 1/0629 600/439 |
| 2011/0054315 A1 | 3/2011 | Roberts et al. | |
| 2011/0088475 A1 | 4/2011 | Oguzman et al. | |
| 2012/0041309 A1 * | 2/2012 | Coussios | A61B 8/08 600/437 |
| 2013/0144165 A1 * | 6/2013 | Ebbini | G01S 7/52046 600/439 |
| 2014/0058294 A1 | 2/2014 | Gross et al. | |
| 2014/0114190 A1 | 4/2014 | Chiang et al. | |
| 2014/0288428 A1 | 9/2014 | Rothberg et al. | |
| 2014/0316269 A1 | 10/2014 | Zhang et al. | |
| 2015/0011880 A1 * | 1/2015 | Kim | A61B 8/14 600/439 |
| 2015/0305821 A1 | 10/2015 | Lacoste et al. | |
| 2016/0000412 A1 * | 1/2016 | Bhuyan | A61B 8/54 600/459 |
| 2019/0076130 A1 | 3/2019 | Bhuyan et al. | |

OTHER PUBLICATIONS

Francis J. Fry, Narendra T. Sanghvi, Richard S. Foster, Richard Bihrle, and Carl Hennige. "Ultrasound and microbubbles: their generation, detection and potential utilization in tissue and organ therapy experimental", Ultrasound in medicine & biology, 21(9): pp. 1227-1237, 1995.

Grondin et al. "Real-time Monitoring of High Intensity Focused Ultrasound (HIFU) Ablation of In Vitro Canine Livers Using Harmonic Motion Imaging for Focused Ultrasound (HMIFU)." Journal of Visualized Experiments. Nov. 2015, pp. 1-7.

Miklos Gyöngy and Constantin-C. Coussios, "Passive cavitation mapping for localization and tracking of bubble dynamics", J. Acoust. Soc. Am. 128 (4), Oct. 2010.

Kennedy et al. "Localization and Interpretation of Bubble Activity during HIFU Exposure." AIP Conference Proceedings 1113, 68 (2009); https://doi.org/10.1063/1.3131473.

Li et al. "A New Active Cavitation Mapping Technique for Pulsed HIFU Applications—Bubble Doppler." *IEEE Trans Ultrason Ferroelectr Freq Control*. Oct. 2014; 61(10): pp. 1698-1708.

J.J. Macoskey, S.W. Choi, T.L. Hall, E. Vlaisavljevich, J.E. Lundt, F.T. Lee Jr, E. Johnsen, C.A. Cain, and Z. Xu, "Using the cavitation collapse time to indicate the extent of histotripsy-induced tissue fractionation", Physics in Medicine & Biology, 63(5):055013, 2018.

Adam D Maxwell, Tzu-Yin Wang, Charles A Cain, J Brian Fowlkes, Oleg A Sapozhnikov, Michael R Bailey, and Zhen Xu, "Cavitation clouds created by shock scattering from bubbles during histotripsy", The Journal of the Acoustical Society of America, 130(4):pp. 1888-1898, 2011.

Zhou, Yu-Feng. "High intensity focused ultrasound in clinical tumor ablation," *World J. Clin. Oncol.* Jan. 10, 2011; 2(1): pp. 8-27.

Jessica E. Parsons, Charles A. Cain, Gerald D. Abrams, and J. Brian Fowlkes, "Pulsed Cavitational Ultrasound Therapy for Controlled Tissue Homogenization", Ultrasound in Medicine & Biology, 32(1): pp. 115-129, 2006.

Vasant A. Salgaonkar, Saurabh Datta, Christy K. Holland, and T. Douglas Mast, "Passive cavitation imaging with ultrasound arrays", J. Acoust. Soc. Am. 126 (6), Dec. 2009.

Armen P. Sarvazyan, Oleg V. Rudenko, Scott D. Swanson, J. Brian Fowlkes, and Stanislav Y. Emelianov, "Shear Wave Elasticity Imaging: A New Ultrasonic Technology of Medical Diagnostics", Ultrasound in Medicine & Biology, 24(9): pp. 1419-1435, 1998.

International Search Report dated Apr. 28, 2020 for International Patent Application No. PCT/US2020/017459.

Written Opinion dated Apr. 28, 2020 for International Patent Application No. PCT/US2020/017459.

* cited by examiner

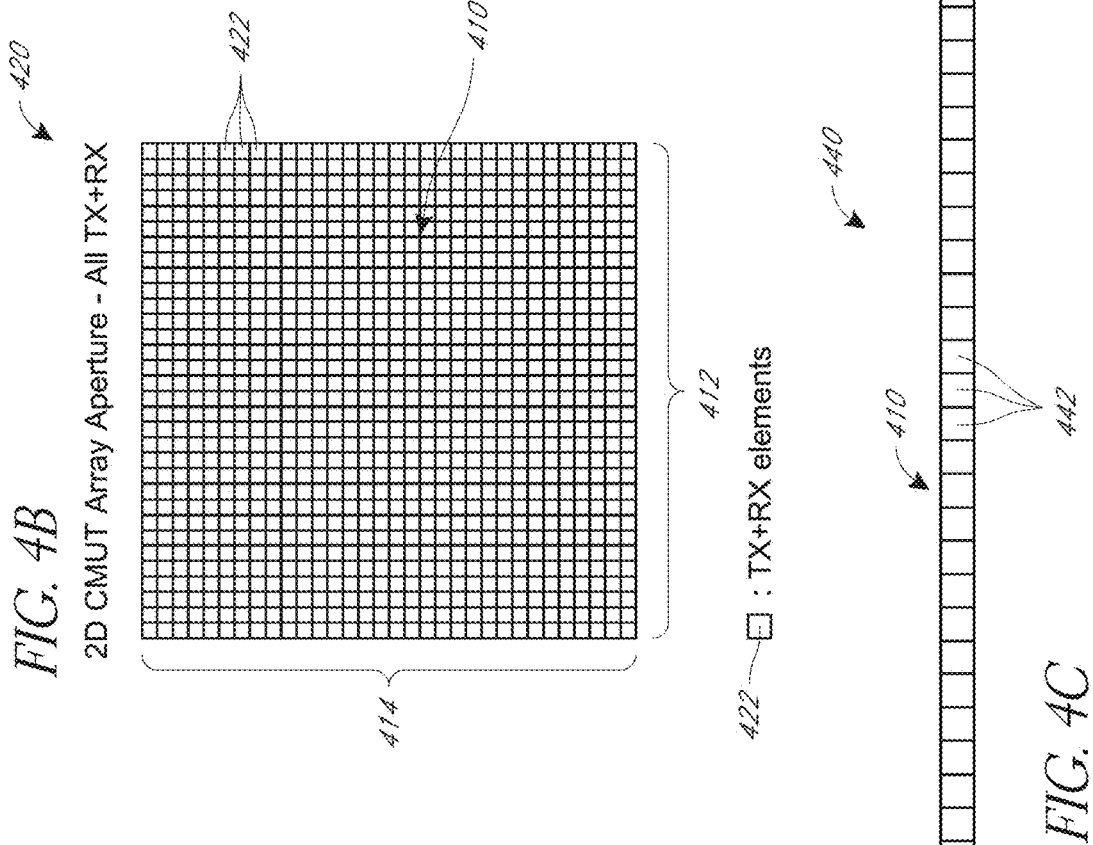
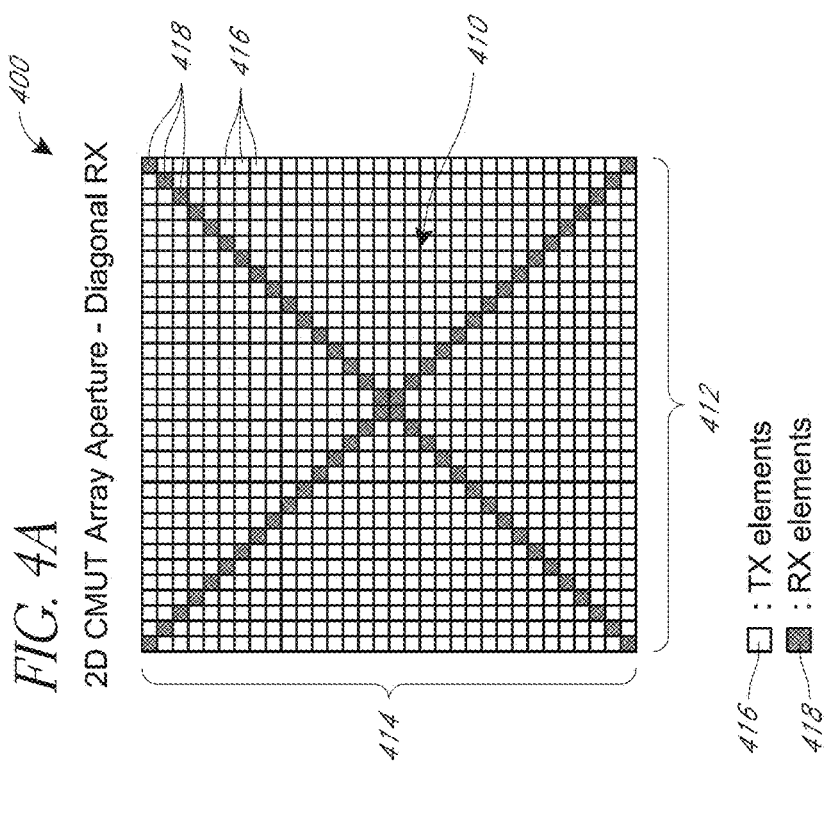
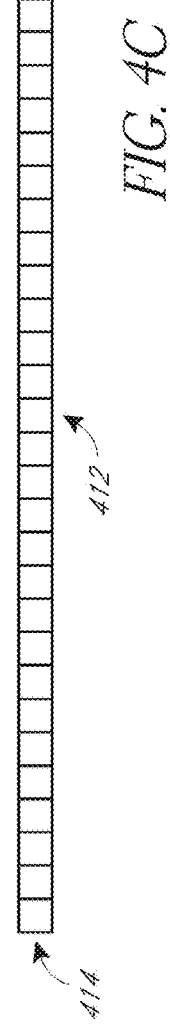

SYSTEMS AND METHODS FOR HIGH INTENSITY FOCUSED ULTRASOUND

CROSS-REFERENCE TO RELATED APPLICATION

Any and all applications for which a foreign or domestic priority claim is identified in the Application Data Sheet as filed with the present application are hereby incorporated by reference under 37 CFR 1.57. For example, this application claims the priority benefit under 35 U.S.C. § 119(e) of U.S. Provisional Application No. 62/804,626, filed Feb. 12, 2019, the entirety of which is hereby incorporated by reference herein for all purposes and forms a part of this specification.

BACKGROUND

Technical Field

This development relates to high intensity focused ultrasound (HIFU), in particular to real-time monitoring of HIFU procedures in certain embodiments.

Description of the Related Art

High intensity focused ultrasound (HIFU) may be used to ablate tissue of the human body. The HIFU may be used, for example, to ablate benign and malignant tumors, such as in the pancreas or prostate, for cosmetic medicine such as treating subcutaneous adipose tissue for the purposes of body contouring, among other uses. Some use of HIFU can be inefficient such that regions of healthy tissue are ablated. Improvements to these and other drawbacks of certain HIFU techniques are desirable.

SUMMARY OF CERTAIN INVENTIVE ASPECTS

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods for high intensity focused ultrasound (HIFU).

The following disclosure describes non-limiting examples of some embodiments. For instance, other embodiments of the disclosed systems and methods may or may not include the features described herein. Moreover, disclosed advantages and benefits can apply only to certain embodiments and should not be used to limit the disclosure. The innovations disclosed herein may be embodied or carried out in a manner that achieves or optimizes one advantage or group of advantages as taught herein without necessarily achieving other advantages as may be taught or suggested herein. Any of the below aspects can be combined with each other as suitable. The present disclosure contemplates combining one or more features of each of the above aspects in each and every suitable combination.

Features for HIFU are described. The application of HIFU for ablating tissue may be monitored in real time by imaging bubbles generated during HIFU. A single transducer array may be used by fast switching between imaging and applying HIFU. For imaging, the array may be used in receive only mode to locate bubbles generated by the HIFU. Alternatively or in addition, a second transducer may perform the imaging. The application of HIFU, such as location or intensity, may be adjusted based on information from the imaging of the bubbles. Physicians may use these systems and methods to monitor HIFU procedures in real-time for optimal ablation of target tissue with minimal damage to healthy tissue. In some embodiments, features alternative to or in addition to bubbles may be imaged using the fast-switching systems and methods described herein.

In one aspect, a method for real-time monitoring of high intensity focused ultrasound (HIFU) ablation is described. The method comprises imaging tissue within a body using an array of ultrasonic transducers, switching between (a) applying HIFU to the tissue using the array, and (b) imaging a bubble of the tissue using the array, the bubble being generated due to the HIFU applied to the tissue, and outputting an indication of the imaged bubble.

The method can further include determining a location of the bubble based on the imaged bubble. Applying HIFU can include applying HIFU to the tissue based on the determined location of the bubble. Determining the location of the bubble can include performing wave-front detection and/or spectral analysis.

Imaging the bubble can include imaging bursting of the bubble. Imaging the bubble can include imaging the bubble after the bubble has collapsed. Imaging the bubble can include B-mode imaging. Imaging the bubble can include harmonic imaging.

The method can include determining a stiffness of the tissue. Determining the stiffness of the tissue can include imaging an indentation of the tissue, in which the indentation is due to applying the HIFU. The method can include determining a time for the tissue to return to an original position after the indentation.

The ultrasonic transducers can be capacitive micromachined ultrasonic transducers (CMUTs).

The method can include imaging the bubble with a second array separate from the first array.

The method can include repeatedly switching between applying the HIFU and imaging the bubble using a plurality of switches coupled with the array. The repeatedly switching can include fast switching. The repeatedly switching can include switching to applying the HIFU after imaging the bubble in no more than two milliseconds. The repeatedly switching can include switching to applying the HIFU after imaging the bubble in no more than one millisecond. The repeatedly switching can include switching to applying the HIFU after imaging the bubble in no more than one microsecond.

Imaging the bubble can include imaging the bubble with the array in a receive-only mode after applying the HIFU.

The method can include determining a measure of HIFU efficacy based on the imaging of the bubble.

The indication of the imaged bubble represent one or more of the following: a size of the bubble, a location of the bubble, a shape of the bubble, an emitted frequency of the bubble, a time of formation of the bubble, and a time of collapse of the bubble.

The method can include presenting a visual signal on a display based on the indication of the imaged bubble. Displaying the visual signal can include displaying the imaged bubble on the display. The method can include emitting an audible signal based on the indication of the bubble.

The tissue can include at least a portion of a prostate with benign prostatic hyperplasia. The tissue can include at least a portion of a uterine fibroid.

In another aspect, a method for real-time monitoring of high intensity focused ultrasound (HIFU) ablation is described. The method includes imaging tissue within a body using an array of capacitive micromachined ultrasonic transducers (CMUTs). The method also includes repeatedly switching between (a) applying HIFU to the tissue using the array and (b) imaging a bubble of the tissue using the array using a plurality of switches. The repeatedly switching includes switching to applying the HIFU after imaging the bubble in no more than two milliseconds. The bubble is generated due to the HIFU applied to the tissue. The method also includes outputting an indication of the imaged bubble.

In another aspect, a system for real-time monitoring of high intensity focused ultrasound (HIFU) ablation is described. The system comprises an array of ultrasonic transducers, a switch, and a processing circuit. The switch is coupled with the array, and the switch is configurable into at least a HIFU mode and an imaging mode. The processing circuit is in communication with the array and the switch. The processing circuit is configured to image tissue within a body using the array, control the switch to change between the HIFU mode and the imaging mode, where the system is configured to apply HIFU to the tissue using the array in the HIFU mode, and where the system is configured to image a bubble of the tissue using the array in the imaging mode, the bubble being generated due to the HIFU applied to the tissue, and the processing circuit is further configured to output an indication of the imaged bubble.

The processing can be configured to determine a location of the bubble based on the imaged bubble. The processing circuit can be configured to apply HIFU to the tissue based on the determined location of the bubble. The processing circuit can be configured to determine the location of the bubble by performing at least one of wave-front detection or spectral analysis.

The processing circuit can be configured to image the bubble bursting. The processing circuit can be configured to image the bubble after the bubble has collapsed. The processing circuit can be configured to image the bubble by at least B-mode imaging. The processing circuit can be configured to image the bubble by at least harmonic imaging.

The processing circuit can be configured to determine a stiffness of the tissue. Determining the stiffness of the tissue can include imaging an indentation of the tissue, the indentation due to applying the HIFU. The processor can be configured to determine a time for the tissue to return to an original position after the indentation.

The array can comprise a capacitive micromachined ultrasonic transducer (CMUT) transducer array.

The system can include a second array of ultrasonic transducers separate from the array and configured to image the bubble.

The system can include a plurality of switches coupled with the array, in which the plurality of switches includes the switch. The processing circuit can be coupled with the plurality of switches and configured for switching the array to the imaging mode using the switches.

The processing circuit can be configured to control the switch to change between the HIFU mode and the imaging mode using fast switching. The processing circuit can be configured to control the switch to change between the HIFU mode and the imaging mode in no more than two milliseconds. The processing circuit can be configured to control the switch to change between the HIFU mode and the imaging mode in no more than one millisecond. The processing circuit can be configured to control the switch to change between the HIFU mode and the imaging mode in no more than five microseconds.

The processing circuit can be configured to image the bubble with the array in a receive only mode after applying the HIFU.

The processing circuit can be configured to determine a measure of HIFU efficacy based on the imaging of the bubble.

The indication of the imaged bubble can represent one or more of a size of the bubble, a location of the bubble, a shape of the bubble, an emitted frequency of the bubble, a time of formation of the bubble, or a time of collapse of the bubble.

The system can include a display configured to present a visual signal based on the indication of the imaged bubble. The processing circuit can cause the display to present the imaged bubble on the display.

The system can include a speaker configured to emit an audible signal based on the indication of the imaged bubble.

In another aspect, a method of ultrasonic ablation and imaging is described. The method comprises applying high intensity focused ultrasound (HIFU) using an ultrasonic transducer array with a switch of the ultrasonic transducer array in a first state, toggling a state of the switch from the first state to a second state in less than five microseconds, and generating an ultrasound image using the ultrasonic transducer array with the switch in the second state.

Toggling can be performed in less than two microseconds. The switch can pass a direct current voltage component and an alternating current voltage component to the ultrasonic transducer array in the first state.

The ultrasonic transducer array can comprise capacitive micromachined ultrasonic transducers (CMUTs). Generating can use receive-only ultrasonic transducers of the ultrasonic transducer array.

In another aspect, a system for ultrasonic ablation and imaging is described. The system comprises an ultrasonic transducer array, a switch, and a processing circuit. The switch is coupled with the ultrasonic transducer array, and the switch is configured to toggle from a first state to a second state. The processing circuit is in communication with the ultrasonic transducer array and the switch. The processing circuit is configured to apply high intensity focused ultrasound (HIFU) using the ultrasonic transducer array with the switch in the first state, toggle the switch from the first state to the second state in less than five microseconds, and generate an ultrasound image using the ultrasonic transducer array with the switch in the second state.

The processing circuit can be configured to toggle the switch in less than two microseconds. The processing circuit can be configured to generate the ultrasound image using receive-only ultrasonic transducers of the ultrasonic transducer array.

The switch can be configured to pass a direct current voltage component and an alternating current voltage component to the ultrasonic transducer array in the first state. The ultrasonic transducer array can comprise capacitive micromachined ultrasonic transducers (CMUTs).

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. It will be understood that elements illustrated in the figures are not necessarily drawn to scale. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure. For example, it will be understood that certain embodiments can include more elements than illustrated in a drawing and/or a subset of the elements illustrated in a drawing. As another example, some embodiments can incorporate any suitable combination of features from two or more drawings.

FIGS. 4A-4C are schematics of transducer array embodiments that may be used with the system of FIG. 1A and/or the method of FIG. 2.

DETAILED DESCRIPTION

Figure 1A:
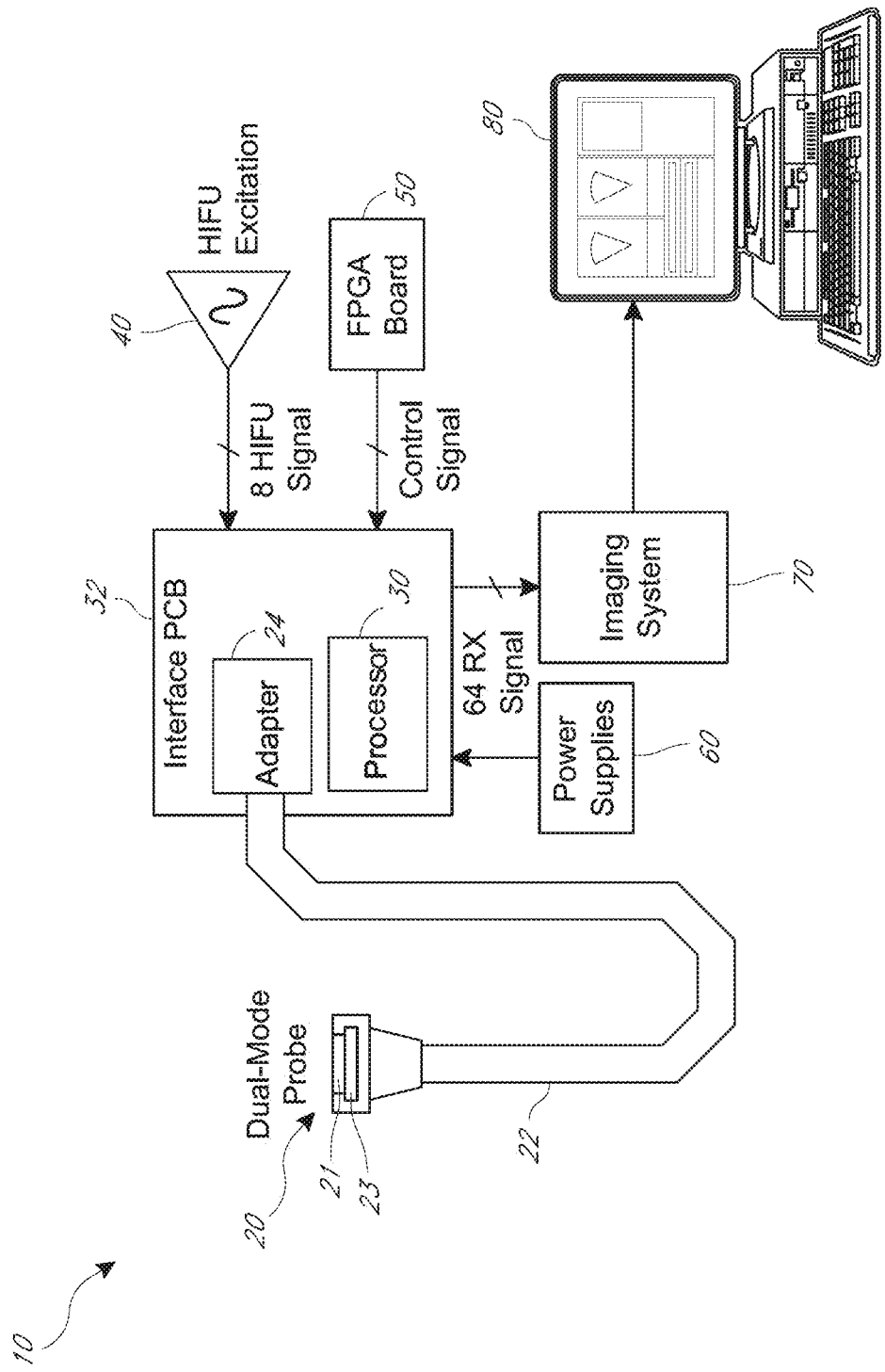
FIG. 1A is a block diagram of an embodiment of a system for applying high intensity focused ultrasound (HIFU).

The following detailed description is directed to certain specific embodiments of the development. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments.

Various embodiments will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the development. Furthermore, embodiments of the development may include several novel features, no single one of which is solely responsible for its desirable attributes or which is essential to practicing the invention described herein.

Some previous uses of high intensity focused ultrasound (HIFU) to ablate tissue have involved blindly applying HIFU or relying on discrete magnetic resonance imaging (MRI) images to track the ablation progress. Such methods of applying HIFU can lead to ablating larger regions than desired. This can involve ablating otherwise healthy surrounding tissue.

Aspects of this disclosure relate to using HIFU to ablate tissue and monitoring progress of the ablation. The progress can be monitored in real-time during a HIFU procedure. The same probe and/or ultrasound transducer array can be used for HIFU and imaging the progress of ablation. Technology disclosed herein can enable a relatively small and/or minimal amount of damage to surrounding tissue while validating the efficacy of a HIFU procedure.

FIG. 1 is a block diagram of an embodiment of a system 10 for high intensity focused ultrasound (HIFU). The system 10 can be used to apply HIFU and monitor the procedure in real-time, for example, by imaging bubbles generated due to HIFU application. The procedure may be monitored by repeatedly switching a transducer array between HIFU application and ultrasonic imaging of the ablated tissue. Using the same array for HIFU and imaging can be advantageous. For example, with the same array, the imaging can have the same line of site as the HIFU. This can involve being directed at the same angle through the same environment to an area of tissue. As further example, with the same array, the probe can be more compact, which may expand the scope of applications. For instance, a small probe could be used for treatment in the throat, such as for sleep apnea treatment or reduction of the tonsils. In some embodiments, a separate outrigger transducer may be used for the imaging.

The system 10 may incorporate an ultrasound diagnostic imaging technique, for example medical ultrasound, diagnostic sonography, or ultrasonography, that is based on the application of ultrasonic waves. Ultrasonic waves have frequencies greater than 20,000 Hz. Ultrasonic waves can have frequencies of up to several gigahertz, for example 1, 2 3, 4, 5 or more gigahertz. The technique may be used to image internal body structures such as one or more of tendons, muscles, joints, blood vessels, and internal organs.

The system 10 may incorporate an ultrasound technique using HIFU that uses ultrasonic waves to heat and/or ablate tissue. The application of HIFU may use relatively lower frequencies as compared with typical ultrasound. A HIFU signal can have a frequency in a range from about 1 megahertz (MHz) to about 100 MHz. The frequency of the HIFU signal can depend on the depth of the region of the tissue that is ablated. For deep lying tissue, about 10 centimeters below the skin, a frequency of 1 MHz can be used. For shallow tissue, a higher frequency, such as 100 MHz can be used. The HIFU may use continuous waves, rather than tone bursts or pulsed waves, to apply desired thermal doses. The HIFU can be used to ablate or destroy tissue, such as tumors, or increase the flow of blood or lymph. The HIFU can be used to treat a range of disorders.

For example, in certain applications the HIFU technique described herein can be used to treat benign prostatic hyperplasia (BPH). In this example, at least a portion of a prostate with BPH can be ablated using HIFU techniques disclosed herein. As another example, in some other applications the HIFU can be used to treat uterine fibroids. In this example, at least a portion of a uterine fibroid can be ablated using HIFU techniques disclosed herein.

The system 10 as shown, using a single transducer array, may be used to repeatedly switch between ultrasonic imaging and applying HIFU to a target tissue. The system 10 may be used to apply the HIFU for ablating tissue and monitoring the ablation in real time by imaging bubbles generated due to application of the HIFU. The application of HIFU, such as location and/or intensity, may be adjusted using the system 10 based on information from the imaging of the bubbles. Physicians and/or other users may use the system 10 and associated methods described herein to monitor HIFU procedures in real-time for improved and/or optimal ablation of target tissue with minimal damage to healthy tissue.

The system 10 includes a probe 20. The probe 20 includes an array 21 of transducers and a circuit 23. The circuit 23 may be an application-specific integrated circuit (ASIC). The array 21 and the circuit 23 may be any of the transducer arrays and circuits, respectively, described herein. The probe 20 may include a capacitive micromachined ultrasonic transducer (CMUT) array 21. A single transducer array 21 may be used with fast switching between imaging and HIFU. The circuit 23 may provide the fast switching. In certain instances, the circuit 23 can include one or more switches arranged to switch the array between HIFU mode and imaging mode. The one or more switches can be circuit switches. For imaging, the array 21 may be used in receive only mode to locate bubbles generated by the HIFU. Alternatively or in addition, a second transducer may perform the imaging. A secondary outrigger transducer array may be used for imaging. In some embodiments, particular transducers on the HIFU array may be used as outrigger transducers for imaging only. The array or arrays may therefore have a variety of embodiments, such as those shown and described with respect to FIGS. 1B, 4A-4C and 5. In some embodiments, the probe 20 may be in a water bath.

The system 10 includes a processor 30. The processor 30 can include any suitable circuitry. The processor 30 is shown on a printed circuit board (PCB) 32. An adapter 24 on the PCB 32 connects with the probe 20 via a cable 22. The PCB 32 can include any suitable wired connections. In some other embodiments, the probe 20 may wirelessly communicate with the processor 30 and/or adapter 24. The processor 30 may store instructions that when executed by the processor 30 cause the system 10 to ultrasonically image tissue, apply HIFU to tissue, and switch back and forth between imaging and applying HIFU. A processing circuit can include the processor 30 and the imaging system 70. In some instances, the processing circuit can also include the integrated circuit on an integrated circuit board 50. In certain instances, the processing circuit can include the imaging system 70 and the integrated circuit on the integrated circuit board 50. The processing circuit can be implemented by physical circuitry in a variety of ways to perform the functions described herein.

The system 10 includes a pulser 40. The pulser 40 may generate a HIFU signal to apply HIFU excitation to the probe 20 via the processor 30. An integrated circuit (IC), such as the field programmable gate array (FPGA), may provide control signals to the processor 30 and/or the circuit 23 for controlling the application of HIFU and imaging with the probe 20. The integrated circuit board 50 can be an FPGA board as shown. Other arrangements and features for signal processing may be used, for example as shown and described with respect to FIG. 5.

The system 10 includes a power system 60 for supplying power to the processor 30 and the probe 20 and other electronics. The power system 60 may include batteries, for example with a portable system 10. The power system 60 may be wall power into which the system 10 is connected.

The system 10 includes an imaging system 70. The processor 30 may transmit, by wire or wirelessly, data regarding the imaged bubbles to the imaging system 70. The data may include one or more received imaging signals based on outputs from the ultrasonic transducers of the array on the probe 20. As shown, there are sixty-four (64) imaging signals received, for example analog signals that are digitized in the imaging system 70. There may be a corresponding number of imaging transducers in the array of the probe 20 each generating one of the signals. In some embodiments, there may be fewer or greater than sixty-four signals and/or transducers for imaging, as further described herein, for example with respect to FIGS. 4A-4C. The data may be analyzed to identify, locate, etc. one or more of the bubbles, or one or more groups of the bubbles, generated due to the HIFU ablation of the tissue.

The system 10 includes a display 80. The imaging system 70 provides the image data and/or image analysis results to the display 80. The display 80 may be on a monitor separate from other elements of the system 10. The display 80 may indicate the location of the bubbles for use in real-time monitoring of the application of HIFU, as further described herein, for example with respect to FIG. 2. An operator, such as a physician, may use the visual data on the display 80 to monitor the HIFU and adjust the HIFU, for example location, intensity, the like, or any suitable combination thereof as desired based on the particular procedure.

The display 80 may show ultrasonic images, for example sonograms, produced by sending waves, for example in pulses, of ultrasound into tissue using the probe 20. In some instances, the ultrasonic images can be three-dimensional (3D). The ultrasound waves bounce off the tissue and/or bubbles, with the tissue and/or bubbles reflecting back various echoes. The bubbles themselves may also self-generate detectable frequencies, such as when the bubbles collapse. These echoes or generated frequencies can be detected and recorded by the imaging system 70. Imaging of the bubbles may include detecting these self-generated frequencies due to bubble collapse or bursting. An indication of the echoes can be displayed as an image on the display 80. The images may be used to locate the bubbles. Different types of images may be formed. In some embodiments, a B-mode image is produced. The B-mode image may display the acoustic impedance of a two-dimensional cross-section of the tissue and/or bubble. Other types of images may be used. In some embodiments, harmonic imaging may be used. Alternatively or additionally, a different interface than a display can present an indication of the bubble to a user. For instance, a speaker can present sound to the user regarding the location of ablation associated with HIFU. As another example, a HIFU probe can vibrate in response to HIFU being directed outside of a target area.

An indication of HIFU bubbles can be provided to a user. Then the user can continue application of HIFU and/or make an adjustment in response to the indication of the HIFU bubbles. For example, the user can direct HIFU to one or more of a different direction, a different angle, or a different tissue depth. The probe 20 can be moved left, right, up and/or down in response to the indication of the HIFU bubbles. In some embodiments, the system 10 may automatically stop the HIFU treatment if the system 10 detects bubbles outside the target area or in an area already treated. The system 10 may keep track of the HIFU dose applied based on the bubbles produced and ensure that no area is over treated. In some instances, a warning can be provided if these and/or any other conditions occur. For example a warning could be generated when HIFU is being applied at, near, or outside a boundary of a tissue region to be ablated, or in a region of prior treatment, etc. Such a warning can include one or more of a beep presented to a user, vibration of the probe 20, or an image on a display 80 changing color. Alternatively or additionally, a similar indication can be provided when HIFU is applied to the same area more than one time and/or for more than a threshold amount of time.

In some embodiments, the system 10 may use other biological information in addition to bubbles for monitoring the HIFU. For example, the imaging may indicate one or more of the stiffness of tissue, the motion of the tissue over time, indentations of the tissue, the flow of blood, the location of blood, the presence of specific molecules, the anatomy of a three-dimensional region, and/or other biological features. Any or all of these features may also be used in addition to bubble imaging to monitor the HIFU application.

Various embodiments of the system 10 may be used. In some embodiments, the system 10 incorporates a CMUT based integrated ultrasound imaging and HIFU delivery system that incorporates fast semiconductor and/or micro-electro-mechanical system (MEMS) switches integrated into the ASIC that can switch direct current (DC) and alternating current (AC) voltages of the system 10 between HIFU and imaging modes in sub-microseconds. Such switches can be referred to as circuit switches. The array 21 being a CMUT array may provide desirable features for the system 10. For example, the CMUT array may provide advantages with regard to decreased heat generation and/or improved heat dissipation, to increased bandwidth for data collection and transmission, and/or to construction for instance without using epoxy bonds as may be used in other array types, such as piezoelectric transducer arrays.

In some embodiments, the system 10 uses a CMUT array that operates in receive-only mode after fast-switching for an imaging mode. In some embodiments, the system 10 includes and/or uses specific instructions stored in non-transitory computer readable storage that solves the back-propagation problem based on wave-front detection using the CMUT array in receive-only mode, and locates and quantifies the bubble dissipation. In some embodiments, the system 10 applies spectral analysis to separate bubble signals from clutter or noise. In some embodiments, the system 10 incorporates a separate (outrigger) transducer or transducer array to perform the bubble localization. In some embodiments, the system includes a CMUT array that is used in pulse-echo imaging mode after fast-switching to an imaging mode. In some embodiments, the system 10 uses conventional B-mode imaging, and harmonic imaging techniques such as pulse inversion, complex pulse sequence, and/or coded excitation are used to locate and quantify bubbles. In some embodiments, the system 10 uses radiation force imaging to quantify the tissue elasticity to monitor HIFU efficacy. In some embodiments, the system 10 uses an outrigger transducer to preform radiation force imaging to monitor HIFU efficacy. In some embodiments, the system 10 uses an outrigger transducer to preform Doppler flow imaging to monitor HIFU efficacy. In some embodiments, the system 10 continuously fast-switches back and forth between HIFU and imaging modes to detect bubble generation and HIFU progression between HIFU bursts or pulses. In some embodiments, the system 10 uses an outrigger transducer simultaneously with the imaging/HIFU probe to detect bubble generation and HIFU progression continuously.

Figure 1B:
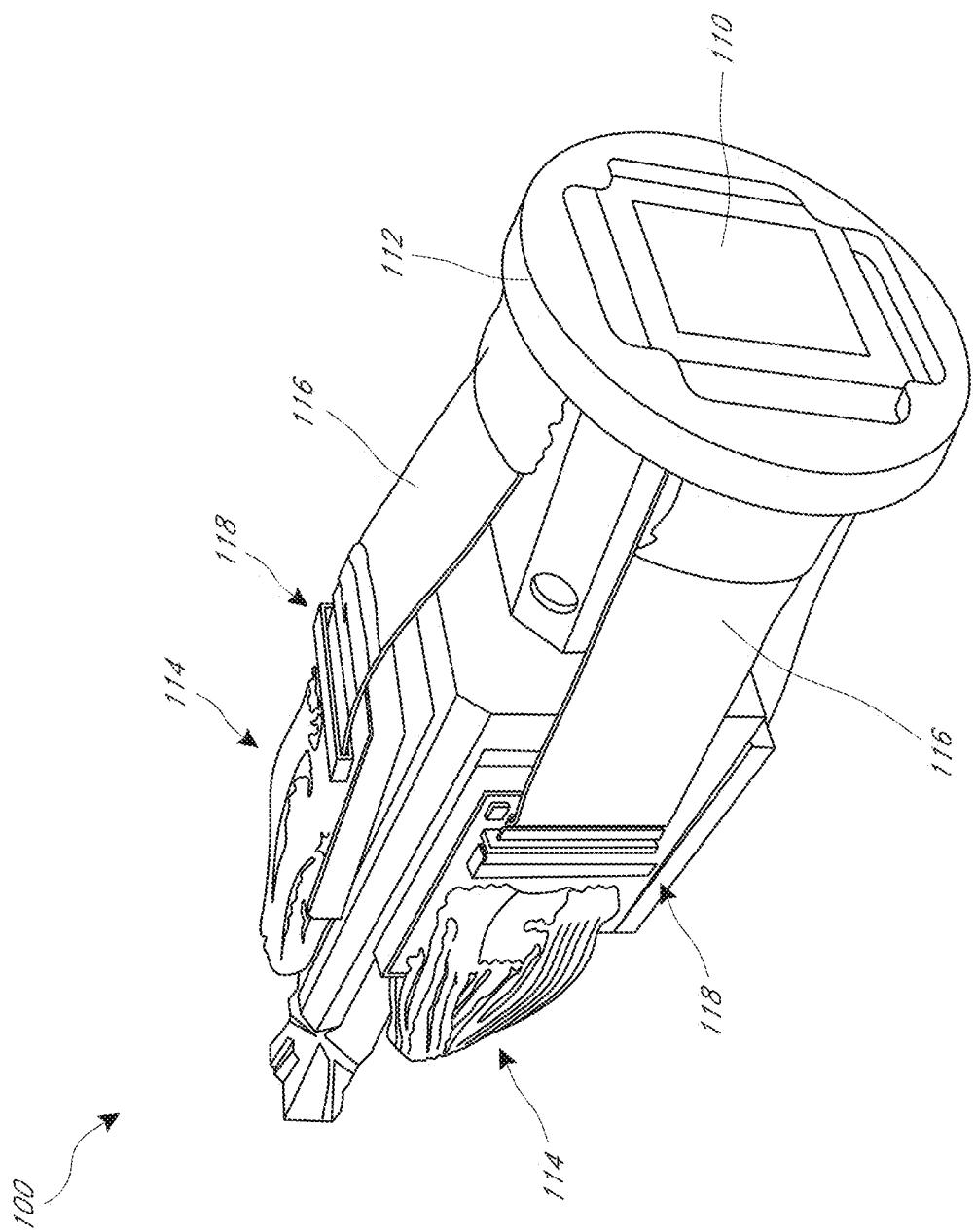
FIG. 1B is a perspective view of an embodiment of a probe having an array of transducers that may be used in the system of FIG. 1A.

FIG. 1B is a perspective view of an embodiment of a probe 100. The probe 100 may be used with the system 10. The probe 100 may have the same or similar features and/or functions as the probe 20 described herein with respect to FIG. 1A, and vice versa.

The probe 100 includes an array 110 of transducers. The array 110 can comprise CMUTs and/or any other suitable ultrasonic transducers. The array 110 is on the distal end of the probe 100. In some embodiments, an application specific integrated circuit (ASIC) is flip-chip bonded to a CMUT chip so that the ASIC is immediately below the CMUT chip. The array 110 has a field of view that extends out and away from the array 110 at the distal end of the probe 100. This "end-looking" field of view may be aligned generally along a longitudinal axis defined by the extended body of the probe 100.

In some embodiments, the probe may be "side-looking," for example where the field of view of the array 110 extends at an angle to the longitudinal axis of the probe 100. This angle may be ninety (90) degrees, forty-five (45) degrees, or any other suitable angular amounts. In some embodiments, the probe 100 may use a one-dimensional (1D) array 110. The array 110 may be any of the arrays described herein, for example those shown and described with respect to FIGS. 4A-4C.

The probe 100 includes a cover on the distal end, which has been removed to clearly show the array 110. The cover may encapsulate the probe 20. The cover may be a polydimethylsiloxane (PDMS) encapsulation. The probe 20 may have a width at the proximal end of twenty-two (22) millimeters (mm) or about 22 mm, or any other suitable width.

The probe 100 includes a tip 112 at the distal end. The tip 112 may be a three-dimensional (3D) tip as shown. A flexible printed circuit board (PCB) 116 connects the array 110 to respective connectors 118, shown as micro zero-insertion-force (μZIF) connectors, on a circuit. Coaxial cables 114 extend from the proximal end of the probe 100 to connect the circuit to the processor and/or other imaging and/or support electronics, for example to the processor 30 and imaging system 70 via the cable 22 as shown in FIG. 1A.

Figure 2:
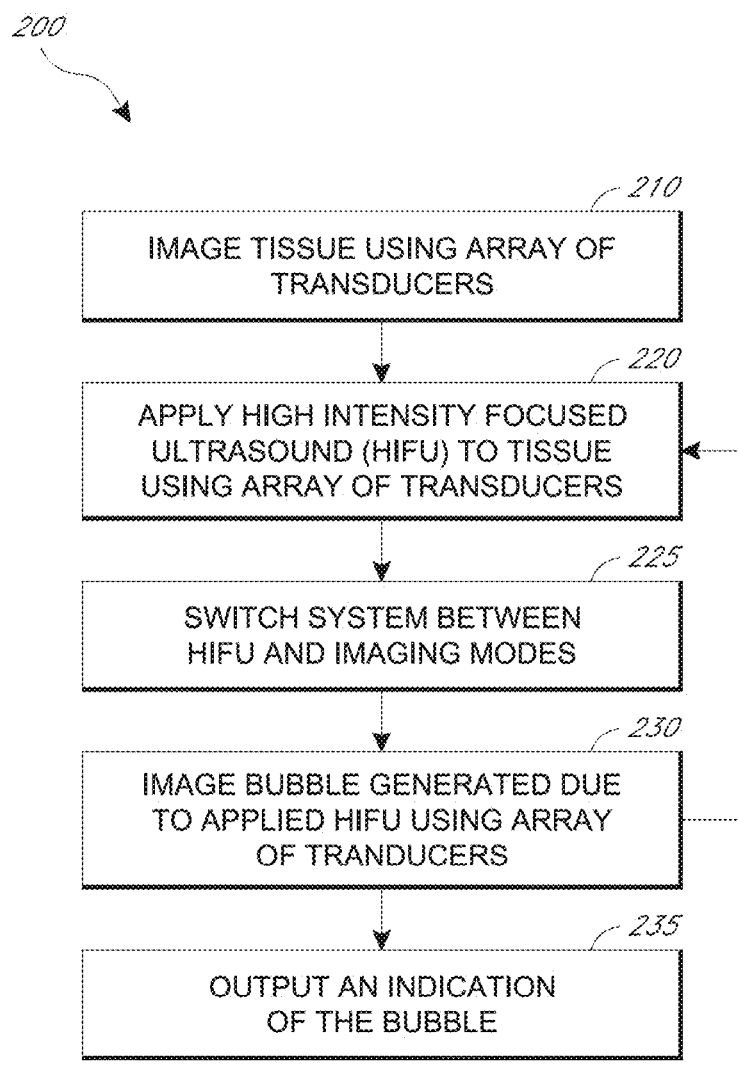
FIG. 2 is a flow chart of an embodiment of a method for applying HIFU that may be performed by the system of FIG. 1A.

FIG. 2 is a flow chart of an embodiment of a method 200 for applying HIFU. The method 200 may be performed by the system 10 and/or probe 100 shown and described with respect to FIGS. 1A-1B. The method 200 may be performed using any of the systems and devices shown and described with respect to FIGS. 3A-6. The method can be performed for a variety of procedures. For example, the method can be performed as part of a tonsillectomy. As another example, the method 200 can be performed as part of a procedure for treating sleep apnea. In certain applications, the method 200 can be performed in a procedure to treat BPH. In some other applications, the method 200 can be performed to treat one or more uterine fibroids. Other medical uses of the method 200 include but are not limited to treating essential tremors, neuropathic pain, Parkinsonian tremor, prostate cancer, solid tumors of the bone, brain, breast, liver, pancreas, rectum, kidney, testes or prostate, palliative treatment of bone metastasis, and others.

The method 200 begins with step 210 wherein tissue is imaged using an array of transducers. The tissue may be any tissue in a human or other animal body. In some embodiments, the tissue is at or near the oral and/or throat regions. The tissue may be in other regions of the body. The tissue may be imaged by placing an ultrasonic probe on the body at or near the target tissue and activating the system 10 for the imaging procedure. The probe 20 or 100 may be used. The array 110 may be used to image the tissue. Some or all of the transducers of the array may be used for imaging. Other arrangements and embodiments of transducers may be used, for example those shown and described with respect to FIGS. 4A-4C. The imaging system 70 may receive and analyze the image data and the display 80 may display the imaging results to an operator. Step 210 may be performed and repeated as desired until the desired target tissue is identified and located.

The method 200 then moves to step 220 wherein HIFU is applied to the target tissue using the array of transducers. Step 220 may be performed after imaging the tissue in step 210. Step 210 may be an initial imaging step to orient the probe and generally locate the target tissue. The same array as used for imaging in step 210 may be used for applying the HIFU in step 220. In some embodiments, the same transducers on the same array as used for imaging in step 210 may be used for applying the HIFU in step 220. In some embodiments, the same array but different transducers from those used for imaging in step 210 may be used for applying the HIFU in step 220. In some embodiments, a different array from the array that was used for imaging in step 210 may be used for applying the HIFU in step 220, for example where the imaging is performed with a separate outrigger transducer array.

Step 220 may be repeated later in method 200, for example after step 230, as described below. In step 220, applying HIFU may comprise applying HIFU to the tissue based on the determined location of the bubble in step 230. For example, in step 220 the HIFU may be applied to a different location, at a different intensity, etc. based on feedback resulting from step 230.

After step 220, the method 200 then moves to step 225 wherein the system 10 is switched between HIFU mode and imaging mode. The system 10 may be switched from the HIFU mode to imaging mode by toggling a switch coupled with the array from a first state to a second state. The array may apply HIFU with the switch in the first state and image tissue with the switch in the second state, or vice versa. The switch may be used with the various circuits described herein. The switch can be implemented as shown and described with respect to the circuit in FIG. 6. Step 225 may also be performed after step 230 to switch the system 10 from imaging mode back to HIFU mode.

The method 200 then moves to step 230 wherein bubbles generated due to the applied HIFU are imaged using the array of transducers. The application of HIFU in step 220 may cause bubbles to form due to the ablation of tissue. Such bubbles may be cavitation resulting from the HIFU. Cavitation may include the creation or motion of a gas cavity in the acoustic field due to alternating compression and expansion of the tissue as the ultrasound burst propagates through it. The cavitation may be stable or inertial cavitation. Stable cavitation may include stable oscillation of the size of the bubble when exposed to a low-pressure acoustic field. Inertial cavitation may include violent oscillations of the bubble and rapid growth of the bubble during a rarefaction phase when they reach their size of resonance, which may lead to the violent collapse and destruction of the bubble. The violent collapse may produce shock waves of high pressure (e.g., from about 20,000 bars to about 30,000 bars) and high temperature (e.g., from about 2000K to about 5000 K) in the microenvironment. The oscillating motion of stable cavitation may cause a "microstreaming" effect with rapid movement of fluid near the bubble due to its oscillating motion.

The creation, movement, collapse and other features of such bubbles may cause emission of high frequency signals that are detected by the array of transducers in imaging mode. Such detection may be used to identify, locate, characterize, etc. the bubbles and thus the focus of the HIFU application. Imaging of the bubble may include detecting emitted high frequency signals.

The imaging and subsequent analysis of the bubbles may be performed using a variety of suitable approaches. In some embodiments, passive cavitation detection (PCD) may be used. In some embodiments, B-mode imaging may be used, for example to detect hyper-echo formation. In some embodiments, a various Doppler methods may be used, such as bubble Doppler, color Doppler, pulse inversion Doppler, decorrelation Doppler, other suitable Doppler methods, or combinations thereof.

Various characteristics of the bubbles may be used for verifying and/or adjusting the HIFU application. In some embodiments, the system 10 may spatially map the presence of transient bubbles, determine their sizes, determine the degree of nonlinearity, determine the area of the bubble or bubbles, detect groups, clusters, or distributions of bubbles, determine the time and/or duration of the bubble formation, collapse, etc., and/or identify the type of bubble. In some embodiments, spectral analysis of the received signal may be used to distinguish between inertial cavitation and thermally induced bubble activity, and to track the evolution of either bubble population between HIFU applications. Any suitable combination of features of verifying and/or adjusting HIFU application discloses herein can be implemented together with each other.

Step 230 may include switching the probe from HIFU mode to an imaging mode. In some embodiments, in step 230 the probe switches from HIFU mode to an active imaging mode where the probe both transmits and receives ultrasound, for example as shown and described with respect to FIG. 3A. In some embodiments, in step 230 the probe switches from HIFU mode to a passive imaging mode where the probe both transmits and receives ultrasound, for example as shown and described with respect to FIG. 3B.

Step 230 may be implemented with and/or include a variety of aspects. Step 230 may comprise imaging the bubble with the same array as used in step 220. Step 230 may comprise imaging the bubble with a second array separate from a first array as used in step 220. Step 230 may comprise imaging the bubble with the same array as used in step 210. Step 230 may comprise determining a location of the bubble based on the imaged bubble. Step 230 may comprise imaging the bubble with the array in a receive only mode after applying the HIFU.

In step 230, the system 10 may be fast-switched from HIFU mode to imaging, as further described herein. The imaging array may be used in step 230 in receive only mode to detect bubbles collapsing and identify their locations. In some embodiments, passive source localization techniques may be used in step 230. The distinctive high frequency and broadband signals generated by bubbles, for example when the bubbles collapse, may be detected. In step 230, a wide-band transducer array, for instance a CMUT transducer array, may detect a significant portion of this energy burst and the location of the bubble burst can be inferred in post processing using a variety of suitable approaches. For example, step 230 may use wave-front detection and solving the inverse problem of backpropagation to localize the bubble collapse. As further example, in step 230 spectral analysis may be used to isolate bubble collapse information from clutter or noise generated by the transducer. As further example, in step 230 separate (outrigger) transducers or elements in the array may be used to detect bubble collapse and localize the source. As a further example, in step 230 all of these and/or other suitable approaches, or combinations thereof, may be used between HIFU bursts or pulses to measure and quantify HIFU progression.

In step 230, in some embodiments fast-switching from HIFU to imaging using pulse-echo and harmonic imaging may be used to locate the bubbles before they dissipate. The bubbles may be hyper-echoic. In step 230, B-mode imaging may be used to see the bubbles before they dissipate. In step 230, harmonic imaging techniques such as pulse inversion, complex pulse sequences or coded excitation may be used, for example to suppress clutter to locate bubbles more effectively. In step 220, the HIFU field may create a radiation force pushing the tissue slightly away from the transducer. Thus, in step 230, the relaxation time or time for the tissue to move back to its original position may be measured. This may be used to estimate the tissue stiffness which may be related to HIFU efficacy. In some embodiments, in step 230 an outrigger transducer may be used to measure Doppler flow in the treated region. For example, the stoppage of blood flow may be used as an indicator of HIFU efficacy. As further example, in step 230 all of these and/or other suitable approaches, or combinations thereof, may be performed between HIFU bursts or pulses to measure and/or quantify HIFU progression.

Step 230 may comprise determining a measure of HIFU efficacy and/or efficiency, for example based on the imaging of the bubble. In step 230, locating the bubble may comprise wave-front detection or spectral analysis. In step 230, imaging the bubble may comprise imaging the bubble bursting. In step 230, imaging the bubble may comprise imaging the bubble after it has collapsed. In step 230, imaging the bubble may comprise B-mode imaging. In step 230, imaging the bubble may comprise harmonic imaging. Step 230 may comprise determining a stiffness of the tissue. In step 230, determining the stiffness of the tissue may comprise imaging an indentation of the tissue, the indentation due to applying the HIFU. Step 230 may comprise determining a time for the tissue to return to an original position after the indentation.

In step 230, the processor 30 may analyze the imaging data to determine these and/or other parameters in order to control, and if needed adjust, the HIFU procedure. The control may be automated. The control may be implemented by the operator based on visual feedback on the display 80. The control may include a combination of automatic and manual adjustments to the system 10. Various control systems may be used in the method 200, for example those shown and described with respect to FIGS. 3A and 3B.

After step 230, the method returns to step 220 for further HIFU application. Between steps 230 and 220, the system can be switched from imaging mode to HIFU mode. Step 225 may be performed again between step 230 and 220. Any adjustment to, or continuation of, the applied HIFU may be made or applied by returning to step 220 for application of HIFU after imaging the bubbles in step 230. Step 220 may be repeatedly returned to after step 230 until the HIFU procedure is complete. The method 200 may therefore comprise performing step 220, then step 230, then step 220, then step 230, then step 220, etc. Step 225 may be repeatedly performed between step 230 and 220. In some embodiments, step 210 may be performed once and then steps 220 and 230 repeatedly performed. In some embodiments, step 210 may be performed after repeating steps 220 and 230 to assess the target tissue. Steps 220 and 230 may then be performed again if it is deemed that further HIFU is desired.

The method 200 may therefore comprise repeatedly switching between applying the HIFU in step 220 and imaging the bubble in step 230. Fast electronic switching, such as in step 225, from applying HIFU in step 230 to imaging in step 220 is desired in order to observe dissipation of bubbles generated during HIFU. These bubbles can be used to locate the HIFU focus and evaluate its efficacy, as described. The bubbles dissipate in a matter of microseconds, so a fast switching time of all transducer voltages is therefore significant. In some embodiments, the system 10 of FIG. 1A is used to perform the method 200 and incorporates a CMUT based integrated ultrasound imaging and HIFU delivery system is used that incorporates fast semiconductor or micro-electro-mechanical system (MEMS) switches integrated into the ASIC that can switch direct current (DC) and alternating current (AC) voltages of the system 10 between HIFU and imaging modes in sub-microseconds.

The method 200 may comprise repeatedly switching between step 220 and step 230 using a plurality of switches coupled with the array. The method 200 may comprise switching the array to an imaging mode using the switches. The method 200 may comprise repeatedly switching by repeatedly fast switching. The method 200 may comprise repeatedly fast switching by switching to applying the HIFU after imaging the bubble in no more than a specified threshold time. The threshold time can be an amount of time sufficiently fast to facilitate imaging of bubbles generated from HIFU. The threshold time may be two milliseconds. The threshold time may be one millisecond, one microsecond, or any other suitable thresholds. Such features may be included in step 225.

The threshold time to switch may refer to a first length of time measured from the end of an application of HIFU to the beginning of imaging. Thus, the first length of time may be measured from ending step 220 to beginning step 230. The first length of time may be the duration of step 225. In some embodiments, a second length of time may be measured from the end of an imaging mode to the beginning of an application of HIFU. Thus the second length of time may be measured from ending step 230 to beginning step 220. The second length of time may be the duration of step 225 when step 225 is performed between step 230 and returning to step 220.

In some embodiments, the first length of time is shorter than the second length of time. The first length of time may be no greater than 0.005 seconds, 0.002 seconds, 0.0015 seconds, 0.001 seconds, 0.0005 seconds, 0.00025 seconds, 0.0001 seconds, 0.00001 seconds, or 0.000001 seconds. The first length of time can be in a range from about 0.5 microsecond to about 5 milliseconds.

Switching between HIFU mode and imaging mode takes a non-zero amount of time. Switching between HIFU mode and imaging mode can take at least an amount of time for a switch to toggle between states. As one example, switching can take at least 0.5 microsecond in certain applications.

In some embodiments, steps 230 and 220 may be performed simultaneously and/or with overlapping periods of operation. For example, in step 230 a second outrigger transducer may be used for imaging while HIFU treatment is applied during step 220. During HIFU treatment in step 220, an outrigger transducer may be used in step 230 to detect bubble formation with pulse-echo and harmonic imaging, detect bubble collapse with passive source localization, detect tissue stiffness by measuring tissue displacement, measure Doppler flow in the treated region, detect other suitable parameters, or combinations thereof. The stoppage of blood flow could be used as an indicator of HIFU efficacy.

After step 230, the method 200 may also proceed to step 235 wherein an indication of the bubble is output. In step 235, one or more of various indications of the bubble may be output. The indication of the imaged bubble may be one or more of a size of the bubble, a location of the bubble, a shape of the bubble, an emitted frequency of the bubble, a time of formation of the bubble, or a time of collapse of the bubble. Step 235 may include displaying a visual signal on a display, such as the display 80. The imaged bubble may be displayed on the display. Step 235 may include emitting one or more audible signals. In some embodiments of the method 200, step 235 may be performed after step 230 but before performing step 220. In some embodiments, step 235 may be performed simultaneously with step 220 and/or with step 230.

In some embodiments of the method 200, features in addition or alternative to the bubble may be imaged. For example, step 230 may include imaging tissue features other than the bubble but still incorporate the fast switching techniques described herein. In some embodiments of the method 200, step 220 may include applying HIFU using an ultrasonic transducer array with a switch of the ultrasonic transducer array in a first state, step 225 may include toggling a state of the switch from the first state to a second state in less than five microseconds or other time periods as described herein, and/or step 230 may include generating an ultrasound image using the ultrasonic transducer array with the switch in the second state. The image in step 230 may, as mentioned, be an image of features other than the bubble. The toggling may be performed in less than two microseconds or other time periods described herein. The toggling may be performed in less than any of the threshold times for switching disclosed herein. The toggling can be performed in a non-zero amount of time that is at least an amount of time for the switch to change state. The switch may pass a direct current voltage component and an alternating current voltage component to the ultrasonic transducer array in the first state.

Figure 3A:
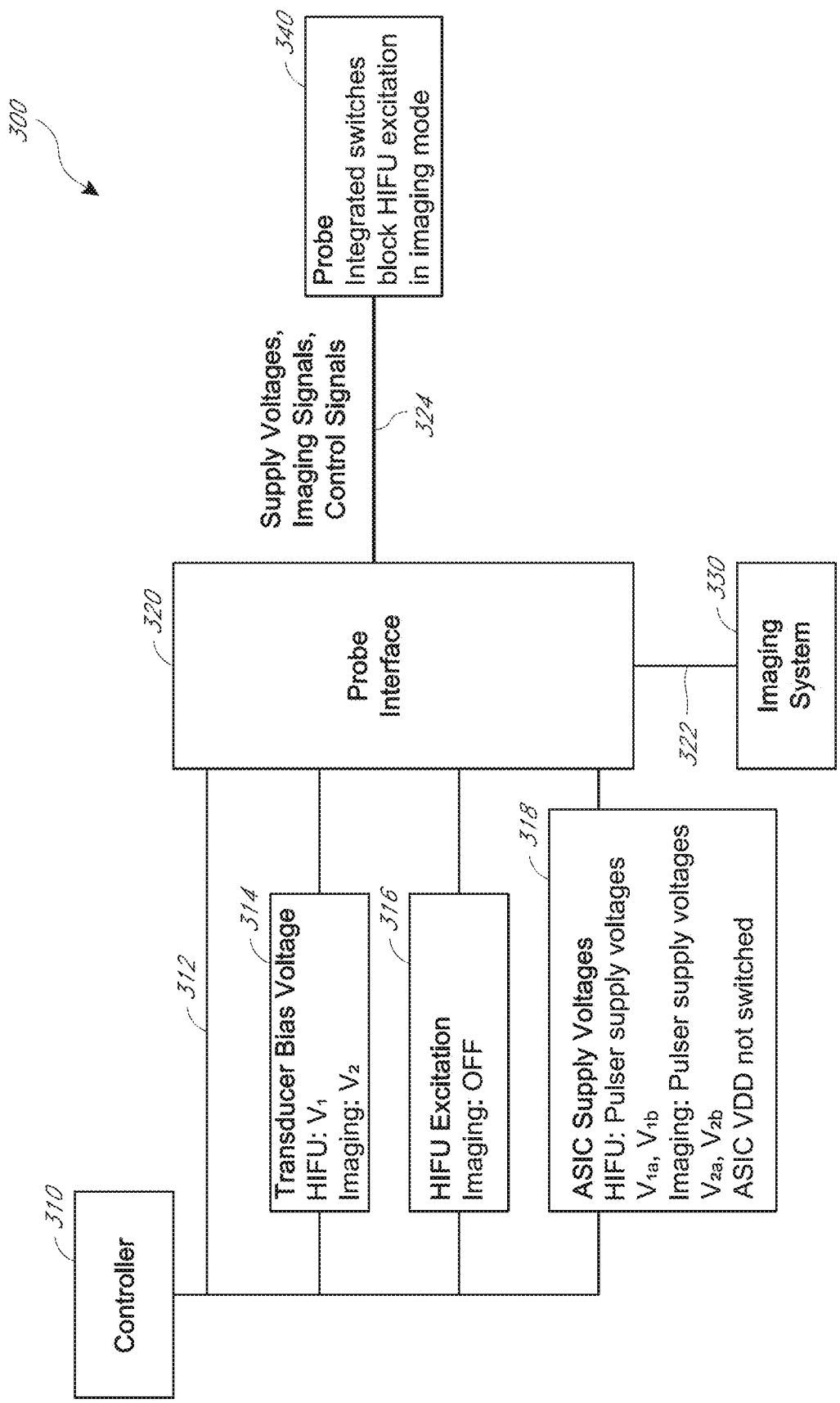
FIG. 3A is a schematic of an embodiment of a control system with active imaging that may be used with the system of FIG. 1A and the method of FIG. 2.
Figure 3B:
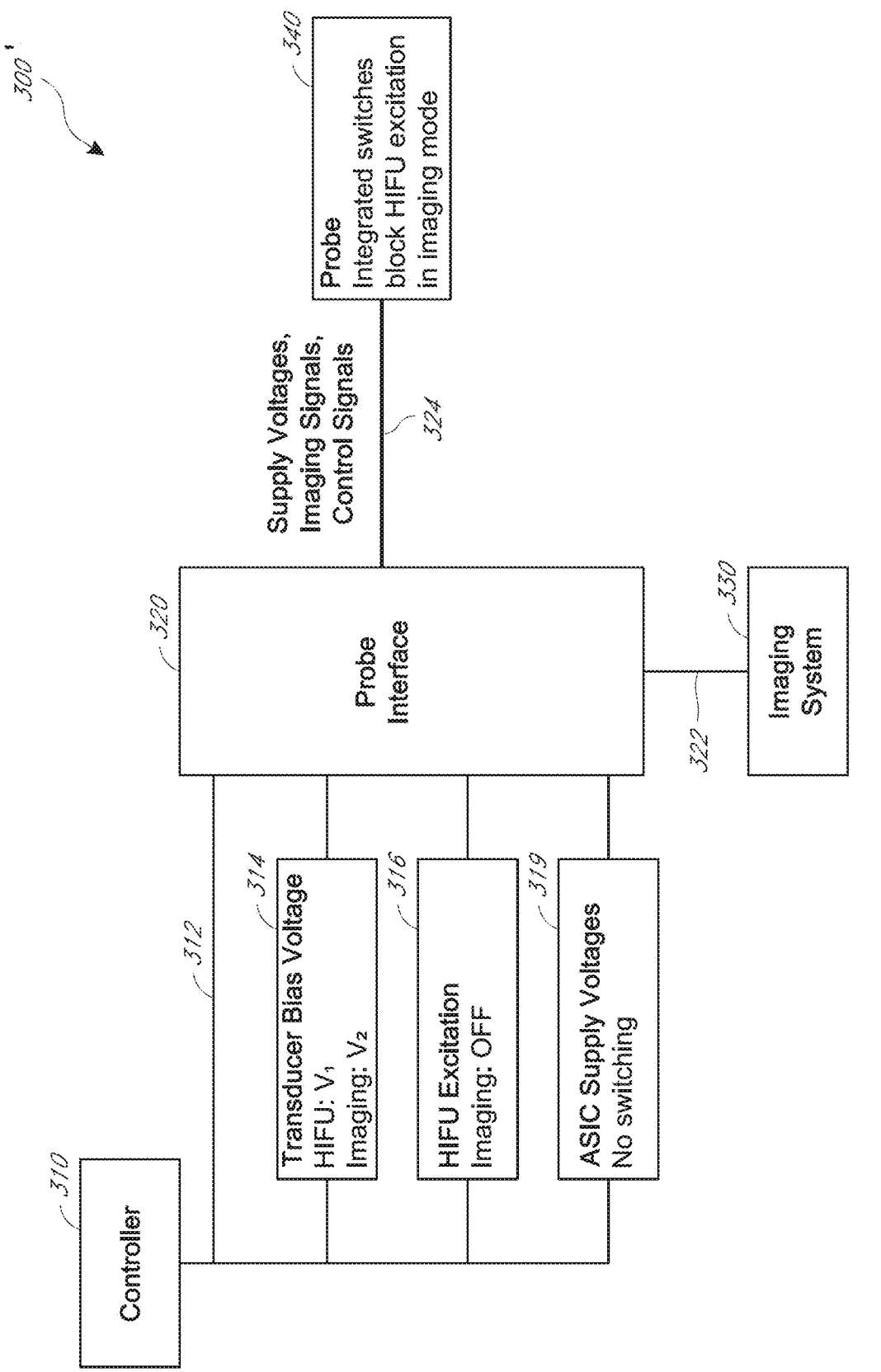
FIG. 3B is a schematic of an embodiment of a control system with passive imaging that may be used with the system of FIG. 1A and/or the method of FIG. 2.

FIGS. 3A-3B are schematic block diagrams of embodiments of a control system 300, 300' that may be used with the system 10 and/or the method 200. FIG. 3A shows the control system 300 using active imaging. FIG. 3B shows the control system 300' using passive imaging.

Referring to FIGS. 3A and 3B, the control system 300, 300' includes a controller 310. The controller 310 may be part of the processor 30 and/or the integrated circuit of the integrated circuit board 50, such as an FPGA. The controller 310 is in communication with a probe interface 320 via connection 312. The controller can provide one or more control signals for the probe interface 320 via the connection 312. The controller 310 provides control signals and/or commands to control a transducer bias voltage circuit 314, a HIFU excitation circuit 316, and a supply voltage circuit 318 each of which are configured to apply a respective signals to the probe interface 320. The controller 310 provides control signals to set the transducer bias voltage circuit 314 values for applying HIFU and for imaging. For example, the transducer bias voltage circuit 314 can provide a bias voltage $V_1$ to transducers of the probe 340 in HIFU mode and bias voltage $V_2$ to transducers of the probe 340 in imaging mode, in which bias voltage $V_1$ is greater than bias voltage $V_2$. The controller 310 provides one or more control signals to set the HIFU excitation circuit 316 mode such that HIFU is "on" and imaging is "off" in HIFU mode.

As shown in FIG. 3A, the controller 310 provides control signals to the supply voltage circuit 318 to set the supply voltages for HIFU and imaging. In this approach, the controller 300 switches from HIFU mode to an imaging mode where the probe 340 both transmits and receives ultrasound. In some embodiments, the bias voltage of the CMUT is switched, for example to use different and/or optimal bias voltages in both HIFU and imaging modes. The supply voltage circuit 318 can provide supply voltages $V_{1A}$ and $V_{1B}$ to pulsers in HIFU mode and supply voltages $V_{2A}$ and $V_{2B}$ to pulsers in imaging mode. The supply voltage circuit can provide an ASIC supply voltage $V_{DD}$ that in not switched.

As shown in FIG. 3B, the supply voltages are not switched by a supply voltage circuit 319 in the control system 300'. In this approach, the controller 310 switches from HIFU mode to an alternate imaging mode in which the probe 340 only receives ultrasound and does not transmit ultrasound. This mode may be used to detect and/or localize the collapse of bubbles created from HIFU mode.

In some embodiments, the controller 310 may switch between passive and active imaging. For example, after a relatively short period of passive imaging, the system can switch over to active imaging.

As further shown in FIGS. 3A and 3B, the control signals from the controller 310 are provided to a probe interface 320. The probe interface 320 may include some or all of the processor and circuitry for controlling the probe 340 and for processing the received signals. The probe interface 320 may include the same or similar features and/or functions as the processor 30 shown and described with respect to FIG. 1A. The probe interface 320 may be part of the probe 100 shown and described with respect to FIG. 1B. The probe interface 320 is connected to the imaging system 330 via connection 322 and to the probe 340 via connection 324. The imaging system 330 may have the same or similar features and/or functions as the imaging system 70 shown and described with respect to FIG. 1A. The probe 340 may have the same or similar features and/or functions as the probes 20 and/or 100 shown and described with respect to FIGS. 1A and 1B respectively. The probe 340 may include integrated switches to block HIFU excitation while the probe 340 is in imaging mode. The probe 340 can receive supply voltages, imaging signals, and control signals via the connection 324.

FIGS. 4A-4C are schematic end views of embodiments of arrays 400, 420, 440 of transducers that may be used with the system 10, for example the part of the probe 20, and/or in the method 200, as shown and described with respect to FIGS. 1A and 2 respectively. Any or all of the arrays 400, 420, 440 may be used with the probe 100 as shown and described with respect to FIG. 1B. Any or all of the arrays 400, 420, 440 may be used with the probe 340 as shown and described with respect to FIGS. 3A-3B. The arrays 400, 420, 440 can transmit and receive ultrasound signals. The illustrated arrays 400, 420, 440 can be CMUT arrays, for example.

FIGS. 4A and 4B show embodiments of two-dimensional (2D) arrays 400, 420 having a plurality of transducer elements 410. The transducer elements 410 include rows 412 and transverse columns 414. As illustrated, each row 412 and column 414 includes thirty-two (32) transducer elements 410. In some embodiments, each row 412 and/or column 414 may include fewer or greater than 32 transducer elements 410, such as a 1024×1024 pixel array. In some embodiments, a single row 412 may include more elements than a single column 414, or vice versa. The arrays 400, 420 may have a square, rectangular, or any other suitable shape.

As shown in FIG. 4A, the transducer elements 410 of the array 400 include dedicated transmitting (Tx) transducer elements 416 and dedicated receiving (Rx) transducer elements 418. For clarity, only some of each of the Tx transducer elements 416 and Rx transducer elements 418 are labelled in FIG. 4A. The Rx transducer elements 418 are arranged in a diagonal pattern resembling an "X" shape, with the remaining transducer elements 410 of the array 400 being Tx transducer elements 416. This is one example and a variety of different suitable patterns may be implemented for the Tx transducer elements 416 and/or the Rx transducer elements 418, such as row or column patterns, patterns with every other row or column, patterns with multiple diagonal lines, patterns with "thicker" lines having two or more adjacent similar elements, concentric, circular or other non-linear patterns, etc. In some embodiments, the array 400 may include some "hybrid" transducer elements that both transmit and receive, as described with respect to FIG. 4B. The various patterns may be scaled proportionally for a given array size, such as a 1024×1024 pixel array. For example, there may be sixty-four (64) Rx transducer elements 418 and nine-hundred and sixty (960) Tx transducer elements 416.

As shown in FIG. 4B, the transducer elements 410 of the array 420 includes hybrid transmitting (Tx) and receiving (Rx) transducer elements 422. For clarity, only some of the elements 422 are labelled in FIG. 4B. Each of the transducer elements 410 can therefore be used for transmitting and for receiving. This is one example and a variety of different suitable patterns may be implemented for the elements 422, such as diagonals (for example, as shown in FIG. 4A), row or column patterns, patterns with every other row or column, patterns with multiple diagonal lines, patterns with "thicker" lines having two or more adjacent similar elements, concentric, circular or other non-linear patterns, etc. A subset of transducer elements 410 can transmit and receive in certain applications. Transducer elements can transmit and receive in some modes of a system and in other modes some or all transducer elements can be transmit only and/or receive only. In some embodiments, the array 420 may include some dedicated elements that either only transmit or only receive, as described with respect to FIG. 4A.

FIG. 4C shows an embodiment of a one-dimensional (1D) array 440 having a plurality of transducer elements 410. The transducer elements 410 include the single row 412 and multiple columns 414. As illustrated, there are fifty (50) of the elements 410, i.e. 50 of the columns 414. In some embodiments, there may be fewer or greater than 50 of the transducer elements 410. In some embodiments, there may be one of the columns 414 and multiple rows 412. As shown, the transducer elements 410 are all "hybrid" transmitting (Tx) and receiving (Rx) transducer elements 442. For clarity, only some of the elements 442 are labelled in FIG. 4C. Each of the transducer elements 410 can therefore be used for transmitting and for receiving. This is one example and a variety of different suitable patterns may be implemented for the elements 442, such as row or column patterns, patterns with every other row or column, with "thicker" lines having two or more adjacent similar elements, concentric, non-uniform spacing, etc. In some embodiments, the array 440 may include some dedicated elements that either only transmit or only receive, as described with respect to FIG. 4A.

Figure 5:
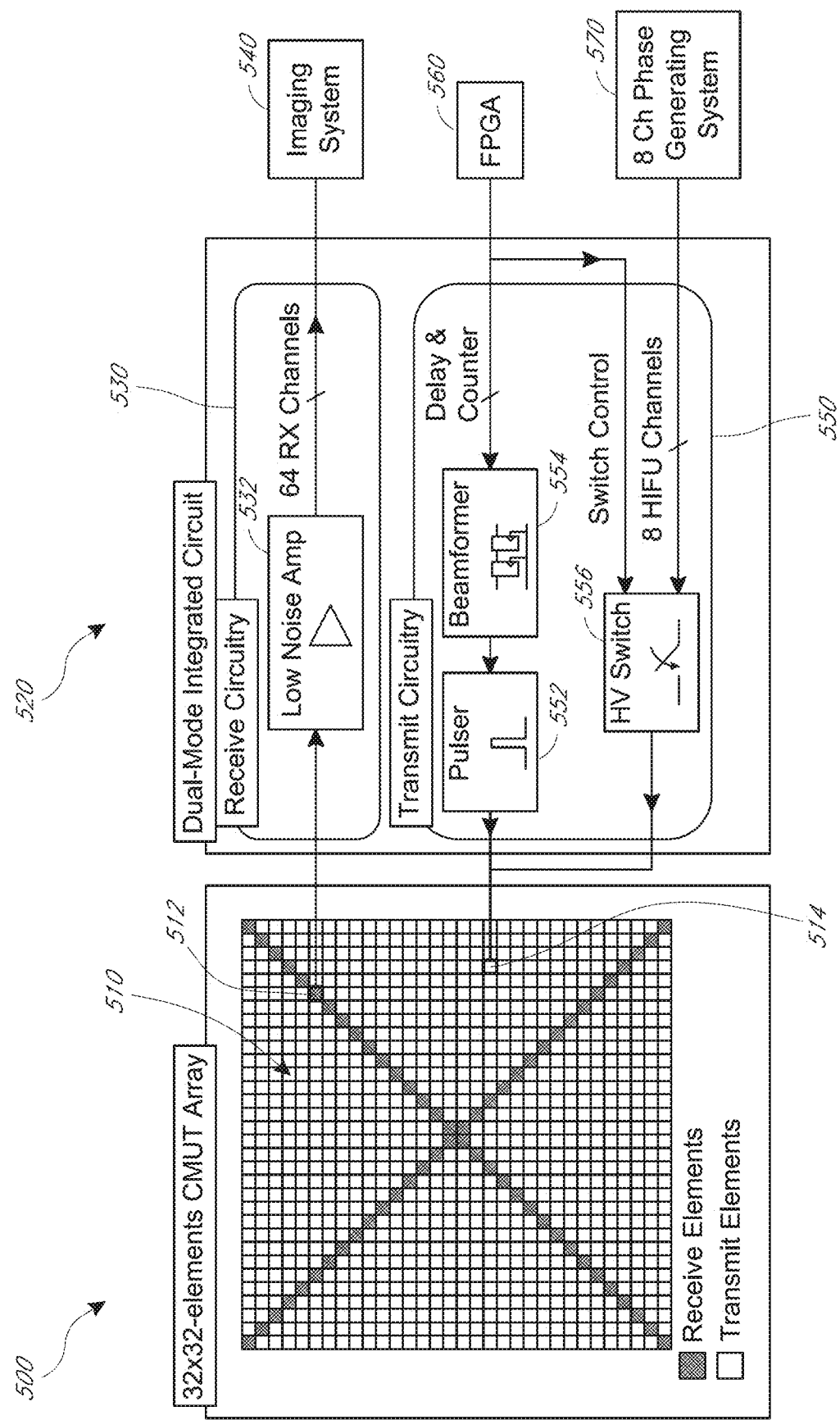
FIG. 5 is a schematic of an embodiment of an integrated circuit (IC) that may be used with the array of transducers of FIG. 4A.

FIG. 5 is a schematic of an embodiment of an ultrasound system that includes an array 500 of ultrasound transducers and a dual-mode integrated circuit (IC) 520 that may be used with the array 500 of transducers. The array 500 is shown as similar to the array 400 of FIG. 4A, although any other suitable array may be used. The array 500 can include CMUTs, for example. As shown, the array 500 has a plurality of dedicated transducer elements 510 that includes receive (Rx) transducer elements 512 in a diagonal pattern with the remaining transducer elements 510 being transmit (Tx) transducer elements 514. A processing circuit that is in communication with the a high voltage switch 556 and the array 500 can include circuitry of the IC 520, an imaging system 540, a control circuit such as an FPGA 560, a phase generating system 570, the like, or any suitable combination thereof.

Circuitry of the IC 520 is shown for each type of transducer element 512, 514. The IC 520 includes receive circuitry 530 for the Rx transducer elements 512. A signal from a Rx transducer element 512 is provided to a low noise amplifier 532. There may be 64 Rx channels as shown. The signal is then sent to an imaging system 540 for imaging. The imaging system 540 may have the same or similar features and/or functions as other imaging systems described herein, such as the imaging system 70 of FIG. 1A and/or imaging system 330 of FIGS. 3A-3B.

The IC 520 includes transmit circuitry 550 for the Tx transducer elements 514. An FPGA 560 can transmit a signal to a beamformer 554. The beamformer 554 can be a spatial filter that processes the signal to provide directional signal transmission. The signal is then transmitted to a pulser 552. The pulser 552 modifies the waveform to provide a pulsing signal to the Tx transducer element 514. A phase generating system 570 transmits a signal to a high voltage (HV) switch 556. The phase generating system 570 may be an eight (8) channel system as shown to provide 8 HIFU channels. A signal from the FPGA 560 is also transmitted to the HV switch 556. The HV switch 556 controls the transmission of HIFU signals to the Tx transducer element 514. The HV switch 556 can pass a HIFU signal from the phase generating system 570 to the array 500 in a HIFU mode. The HV switch 556 can electrically isolate the phase generating system 570 from the array 500 in an imaging mode. In some embodiments, the FPGA 560 may send the transmit delay/phase for each transmit element to the beamformer 554. The FPGA 560 may have the processing power to keep track of the direction in which the device should sonicate next. The beamformer 554 can communicate with and control each pulser 552 when it is time to fire a pulse. The signal may thus be generated in the pulser 552. The pulser 552 can provide a substantially constant output in the imaging mode.

Figure 6:
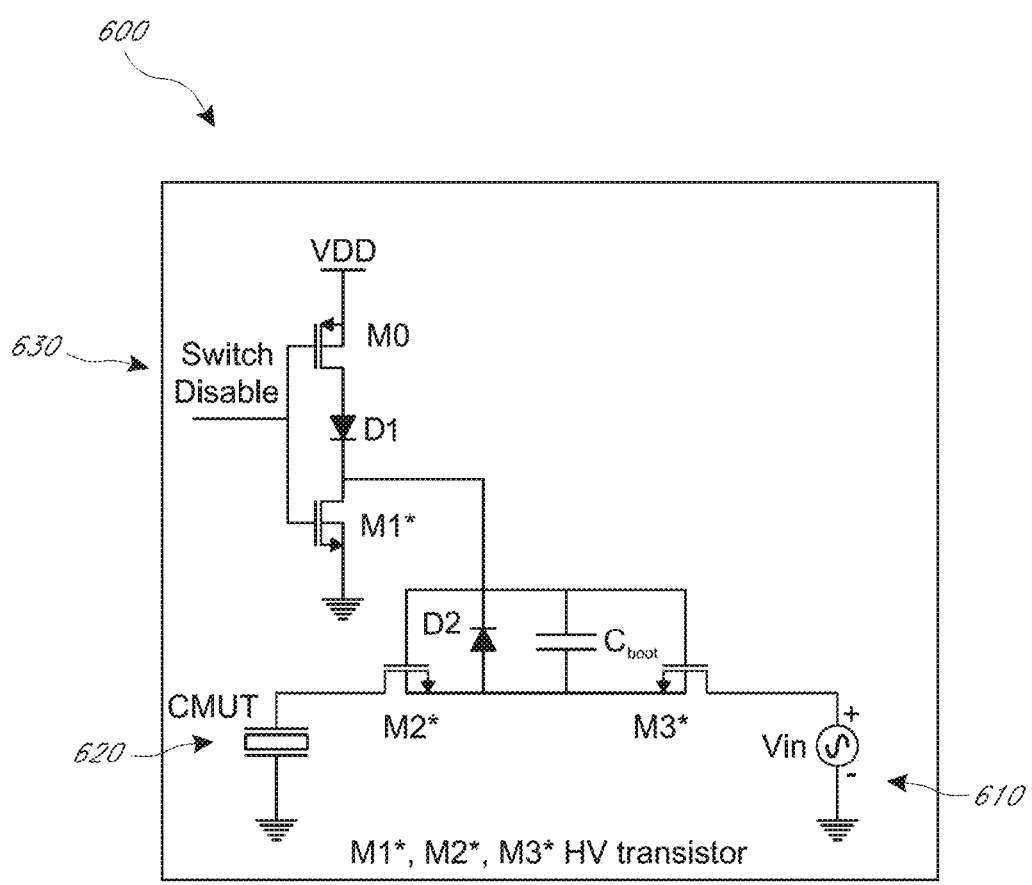
FIG. 6 is a schematic of an embodiment of a circuit that may be used with the system of FIG. 1A and/or the method of FIG. 2.

FIG. 6 is a schematic of an embodiment of a switching circuit 600 that may be used with the system 10 and/or the method 200. The switching circuit 600 may be used to switch between HIFU and imaging modes. The switching circuit 600 includes an input from a pulser 610 and a control input 630 to a switch. The switch can provide the input from the pulser to a transducer 620 of a transducer array. The illustrated transducer 620 is a CMUT. The switching circuit 600 includes a switch that includes transistors M0, M1, M2, and M3, the illustrated diodes D1 and D2, and the capacitor $C_{BOOT}$. Transistors M1, M2, and M3 can be high voltage transistors. Such high voltage transistors can handle voltages provides by the pulser 610. The diode D1 can be a high voltage diode. The transistor M0 and the diode D1 can be low voltage devices. The illustrated transistors M0, M1, M2, and M3 are field effect transistors. In the switching circuit 600, the switch can pass a voltage from the pulser 610 that is great than a gate-to-source voltage minus a threshold voltage of any one of the transistors of the switch. The switch can turn on or off in response to the switch disable signal provided to a control terminal (e.g., a gate as illustrated) of transistors M0 and M1. In one state, the switch provides a voltage from pulser 610 to a CMUT 620 of the array. In another state, the switch electrically isolates the CMUT 620 of the array from the pulser 610.

The flow chart sequences are illustrative only. A person of skill in the art will understand that the steps, decisions, and processes embodied in the flowcharts described herein may be performed in any suitable order other than that described herein. Thus, the particular flowcharts and descriptions are not intended to limit the associated processes to being performed in the specific order described.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others. The scope of the invention is indicated by the appended claims rather than by the foregoing description. All changes which come within the meaning and range of equivalency of the claims are to be embraced within their scope.

The foregoing description details certain embodiments of the systems, devices, and methods disclosed herein. It will be appreciated, however, that no matter how detailed the foregoing appears in text, the systems, devices, and methods may be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment may be included with other depicted embodiments in any combination. For example, any of the various components described herein and/or depicted in the Figures may be combined, interchanged or excluded from other embodiments.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Any and all references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches. For example, terms such as about, approximately, substantially, and the like may represent a percentage relative deviation, in various embodiments, of ±1%, ±5%, ±10%, or ±20%.

The above description discloses several methods and materials of embodiments of the present invention. Embodiments of this invention are amenable to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A method for monitoring of high intensity focused ultrasound (HIFU) ablation, the method comprising:
    imaging tissue within a body using an array of ultrasonic transducers;
    electronically switching a switch for an ultrasonic transducer of the array in no more than five microseconds between (a) a HIFU mode for applying HIFU to the tissue using the array where the switch passes a HIFU signal from a phase generating system to the ultrasonic transducer for applying HIFU to the tissue, and (b) an imaging mode for imaging a bubble of the tissue using the array where the switch electrically isolates the phase generating system from the ultrasonic transducer, the bubble being generated due to the HIFU applied to the tissue, wherein the ultrasonic transducer of the array is used for both the applying HIFU and the imaging the bubble;
    generating an indication of the imaged bubble that is indicative of progress of ablation associated with the applying HIFU, wherein the generating comprises determining a location of the bubble based on the imaging of the bubble; and
    determining a measure of HIFU efficacy based on the indication of the imaged bubble, wherein the applying HIFU comprises applying HIFU to the tissue based on the determined location of the bubble and the determined measure of HIFU efficacy.

2. The method of claim 1, wherein the ultrasonic transducers are capacitive micromachined ultrasonic transducers (CMUTs).

3. The method of claim 1, further comprising repeatedly switching between applying the HIFU and imaging the bubble using a plurality of switches coupled with the array, wherein the repeatedly switching comprises the switching.

4. The method of claim 3, wherein the repeatedly switching comprises switching to applying the HIFU after imaging the bubble in no more than one half of a microsecond.

5. The method of claim 3, wherein the repeatedly switching comprises switching to applying the HIFU after imaging the bubble in no more than one microsecond.

6. The method of claim 1, wherein the imaging the bubble comprises imaging the bubble with the array in a receive-only mode after applying the HIFU.

7. The method of claim 1, further comprising presenting a visual signal on a display based on the indication of the imaged bubble.

8. The method of claim 1, further comprising emitting an audible signal based on the indication of the bubble.

9. The method of claim 1, wherein a plurality of ultrasonic transducers of the array are used for both the applying HIFU and the imaging the bubble.

10. The method of claim 1, further comprising:
    switching to a first system mode where the ultrasonic transducer of the array is used for both the applying HIFU and the imaging the bubble; and
    switching to a second system mode where the ultrasonic transducer of the array is used for transmit only or for receive only.

11. The method of claim 1, wherein the applying HIFU comprises applying HIFU using a control circuit that is in communication with the switch, and wherein the imaging the bubble comprises imaging the bubble using the phase generating system that is in communication with the switch.

12. The method of claim 11, further comprising:
    transmitting a signal, using the control circuit, to a beamformer;
    controlling a pulser using the beamformer when it is time to fire a pulse; and
    modifying a waveform of the signal with the pulser to provide a pulsing signal to the ultrasonic transducer.

13. A system for monitoring of high intensity focused ultrasound (HIFU) ablation, the system comprising:
    an array of ultrasonic transducers;
    a switch coupled with an ultrasonic transducer of the array, the switch configurable into at least a HIFU mode, where the switch passes a HIFU signal from a phase generating system to the ultrasonic transducer for applying HIFU to tissue, and an imaging mode, where the switch electrically isolates the phase generating system from the ultrasonic transducer; and
    a processing circuit in communication with the array and the switch, the processing circuit configured to:
        image tissue within a body using the array;
        control the switch to change between the HIFU mode and the imaging mode in no more than five microseconds, wherein the system is configured to apply HIFU to the tissue using the array in the HIFU mode, wherein the system is configured to image a bubble of the tissue using the array in the imaging mode, the bubble being generated due to the HIFU applied to the tissue, and wherein the ultrasonic transducer of the array is used for both applying HIFU in the HIFU mode and imaging the bubble in the imaging mode;
        generate an indication of the imaged bubble that is indicative of progress of ablation associated with the HIFU mode, wherein to generate the indication the processing circuit is configured to determine a location of the bubble based on the imaging of the bubble;
        determine a measure of HIFU efficacy based on the indication of the imaged bubble; and
        cause HIFU to be applied to the tissue with the ultrasonic transducer based on the determined location of the bubble and the determined measure of HIFU efficacy.

14. The system of claim 13, wherein the array comprises a capacitive micromachined ultrasonic transducer (CMUT) transducer array.

15. The system of claim 13, wherein the processing circuit is configured to control the switch to change between the HIFU mode and the imaging mode in no more than one microsecond.

16. The system of claim 13, wherein a plurality of ultrasonic transducers of the array are used for both applying HIFU in the HIFU mode and imaging the bubble in the imaging mode, the plurality of ultrasonic transducers comprising the ultrasonic transducer.

17. A method of ultrasonic ablation and imaging, the method comprising:

applying high intensity focused ultrasound (HIFU) using a plurality of ultrasonic transducers of an ultrasonic transducer array while a switch coupled to one or more of the plurality of ultrasonic transducers of the ultrasonic transducer array is in a first state;

toggling a state of the switch from the first state to a second state in less than five microseconds;

generating an ultrasound image of a bubble using the plurality of ultrasonic transducers of the ultrasonic transducer array while the switch is in the second state, wherein the ultrasound image of the bubble is indicative of progress of ablation associated with the applying HIFU, and wherein the generating comprises determining a location of the bubble based on the imaging of the bubble, determining a measure of HIFU efficacy based on the ultrasound image of the bubble; and adjusting the applying of HIFU to the tissue based on the determined location of the bubble and the determined measure of HIFU efficacy.

18. The method of claim 17, wherein the toggling is performed in less than two microseconds.

19. The method of claim 17, wherein the switch passes a direct current voltage component and an alternating current voltage component to the ultrasonic transducer array in the first state.

20. The method of claim 17, wherein the ultrasonic transducer array comprises capacitive micromachined ultrasonic transducers (CMUTs).

\* \* \* \* \*